(12) United States Patent
Ono et al.

(10) Patent No.: US 7,153,278 B2
(45) Date of Patent: Dec. 26, 2006

(54) SLEEP APNEA SYNDROME DIAGNOSING DEVICE AND SIGNAL ANALYZER, AND METHODS THEREOF

(75) Inventors: Takahito Ono, Tokyo-to (JP); Takatoshi Yokota, Tokyo-to (JP); Hiroo Yano, Tokyo-to (JP)

(73) Assignee: Kabushiki Kaisha Sato, Tokyo-To (JP)

(*) Notice: Subject to any disclaimer, the term of this patent is extended or adjusted under 35 U.S.C. 154(b) by 322 days.

(21) Appl. No.: 10/800,714

(22) Filed: Mar. 16, 2004

(65) Prior Publication Data
US 2005/0043645 A1    Feb. 24, 2005

(30) Foreign Application Priority Data
Aug. 22, 2003   (JP)    ............... 2003-298401

(51) Int. Cl.
*A61B 7/00* (2006.01)
(52) U.S. Cl. .................. 600/586; 600/324; 600/483
(58) Field of Classification Search ............... 600/301, 600/324, 333, 483, 586, 595
See application file for complete search history.

(56) References Cited

U.S. PATENT DOCUMENTS

| | | | | |
|---|---|---|---|---|
| 3,911,899 A | * | 10/1975 | Hattes | 600/407 |
| 4,365,636 A | * | 12/1982 | Barker | 600/529 |
| 4,617,525 A | * | 10/1986 | Lloyd | 340/573.1 |
| 5,275,159 A | | 1/1994 | Griebel | |
| 5,490,502 A | * | 2/1996 | Rapoport et al. | 128/204.23 |
| 5,549,113 A | * | 8/1996 | Halleck et al. | 600/484 |
| 5,914,660 A | * | 6/1999 | Mesibov et al. | 340/573.7 |
| 5,964,720 A | * | 10/1999 | Pelz | 600/595 |
| 5,989,193 A | * | 11/1999 | Sullivan | 600/534 |
| 6,045,514 A | * | 4/2000 | Raviv et al. | 600/529 |
| 6,142,950 A | * | 11/2000 | Allen et al. | 600/529 |
| 6,280,392 B1 | * | 8/2001 | Yoshimi et al. | 600/534 |
| 6,283,119 B1 | * | 9/2001 | Bourdon | 128/204.23 |
| 6,306,088 B1 | * | 10/2001 | Krausman et al. | 600/301 |
| 6,450,957 B1 | * | 9/2002 | Yoshimi et al. | 600/309 |

FOREIGN PATENT DOCUMENTS

| | | |
|---|---|---|
| DE | 633 097 | 7/1936 |
| EP | 0 006 826 A1 | 1/1980 |
| EP | 2002059082 | 2/2002 |
| GB | 1036604 | 7/1966 |
| JP | 5-200031 | 8/1993 |
| JP | 09220491 | 8/1997 |
| WO | WO 99/30826 A1 | 6/1999 |

OTHER PUBLICATIONS

Thesis of 2003 Spring Meeting of the Acoustical Society of Japan, pp. 425-426, issued Mar. 18, 2003.

(Continued)

*Primary Examiner*—Max F. Hindenburg
*Assistant Examiner*—Rene Towa
(74) *Attorney, Agent, or Firm*—Heller Ehrman LLP

(57) ABSTRACT

A sleep apnea syndrome diagnosing device disclosed herein comprises: a snoring sound collector which collects snoring sound; a snoring sound holder which holds the collected snoring sound; a correlation coefficient calculator which divides a time axis of the snoring sound held in the snoring sound holder into plural cycles and which sequentially calculates a correlation coefficient between the snoring sound of one cycle and the snoring sound of a cycle next to the one cycle; and an output section which outputs the correlation coefficient calculated by the correlation coefficient calculator.

11 Claims, 7 Drawing Sheets

OTHER PUBLICATIONS

Iuga A. et al., "Electrostatic separation of metals and plastics from granular industrial wastes", Industry Applications Conference, 1998, New York.

Kohnlechner R., "Copper Separation from Cable Scrap Ecological Recycling of Cable Scrap", Physics Today, American Institute of Physics., May 1, 1994, pp. 342-343, New York.

* cited by examiner

SLEEP APNEA SYNDROME DIAGNOSING DEVICE AND SIGNAL ANALYZER, AND METHODS THEREOF

BACKGROUND OF THE INVENTION

1. Field of the Invention

The present invention relates to a sleep apnea syndrome diagnosing device and a signal analyzer, and methods thereof.

2. Background Art

It is said that approximately twenty thousand patients with sleep apnea syndrome exist in all of Japan. To check whether the patient has sleep apnea syndrome, it is essential to attach plural different sensors to various parts of a body, such as hands and feet and an abdomen, of the patient and perform a test on the patient, as disclosed in Japanese Patent Laid-open No. Hei 5-200031.

Further, it is necessary for different specialized doctors to analyze test results thus collected, and furthermore it is finally required for these different specialized doctors to gather, bringing their analysis results together, to draw a conclusion as to whether or not the patient has sleep apnea syndrome.

As can be seen from the above, in a related testing method, it is necessary to attach plural sensors to a body of a patient, which causes a problem that the patient finds preparations for a test burdensome. Besides, since the number of necessary sensors is normally 20 or more and these many sensors need to be attached, the explanation and guidance of the test from the doctor to the patient are complicated.

Moreover, after measurement, plural different specialized doctors are required to analyze test results, which causes a problem that a lot of time and cost are necessary. In particular, the analysis of the collected test results requires a lot of time, whereby the development of a method capable of temporary screening in a simple manner is desired. Namely, the development of a method of temporarily screening many patients as to whether they have sleep apnea syndrome, and only when in doubt, performing a more detailed test is desired. In particularly, it is thought that many potential patients exist within Japan, U.S. and so on, whereby it is believed that the development of this screening method is urgently needed.

SUMMARY OF THE INVENTION

Hence, the present invention is made in view of the aforementioned problems, and an object of the present invention is to provide a sleep apnea syndrome diagnosing device and a signal analyzer, and methods thereof.

In order to accomplish the aforementioned and other objects, according to one aspect of the present invention, a sleep apnea syndrome diagnosing device, comprises:

a snoring sound collector which collects snoring sound;

a snoring sound holder which holds the collected snoring sound;

a correlation coefficient calculator which divides a time axis of the snoring sound held in the snoring sound holder into plural cycles and which sequentially calculates a correlation coefficient between the snoring sound of one cycle and the snoring sound of a cycle next to the one cycle; and an output section which outputs the correlation coefficient calculated by the correlation coefficient calculator.

According to another aspect of the present invention, a sleep apnea syndrome diagnosing method, comprises the steps of:

collecting snoring sound and storing the collected snoring sound in a snoring sound holder;

dividing a time axis of the snoring sound held in the snoring sound holder into plural cycles;

sequentially calculating a correlation coefficient between the snoring sound of one cycle and the snoring sound of a cycle next to the one cycle; and outputting the calculated correlation coefficient.

According to another aspect of the present invention, a computer program product including a medium recording a program for diagnosing sleep apnea syndrome, the program being operable to execute the steps of:

collecting snoring sound and storing the collected snoring sound in a snoring sound holder;

dividing a time axis of the snoring sound held in the snoring sound holder into plural cycles;

sequentially calculating a correlation coefficient between the snoring sound of one cycle and the snoring sound of a cycle next to the one cycle; and outputting the calculated correlation coefficient.

According to another aspect of the present invention, a signal analyzer, comprises:

a signal data holder which holds signal data with irregular periodicity;

a correlation coefficient calculator which divides a time axis of the signal data held in the signal data holder into plural cycles and sequentially calculating a correlation coefficient between the signal data of one cycle and the signal data of a cycle next to the one cycle; and an output section which outputs the correlation coefficient calculated by the correlation coefficient calculator.

According to another aspect of the present invention, a signal analyzing method, comprises the steps of:

collecting signal data with irregular periodicity and holding the signal data in a signal data holder;

dividing a time axis of the signal data held in the signal data holder into plural cycles;

sequentially calculating a correlation coefficient between the signal data of one cycle and the signal data of a cycle next to the one cycle; and outputting the calculated correlation coefficient.

DETAILED DESCRIPTION OF THE EMBODIMENTS

Most patients with sleep apnea syndrome snore. Their snoring sound is regular when they normally breathe, but in hypopnea or apnea, the snoring sound is irregular. Therefore, a medical specialist or a clinical laboratory technologist catches changes in this snoring sound by hearing and judges whether or not a patient has sleep apnea syndrome. Hence, this embodiment is intended to analyze the changes in this snoring sound quantitatively. A more detailed explanation will be given below.

Figure 1:
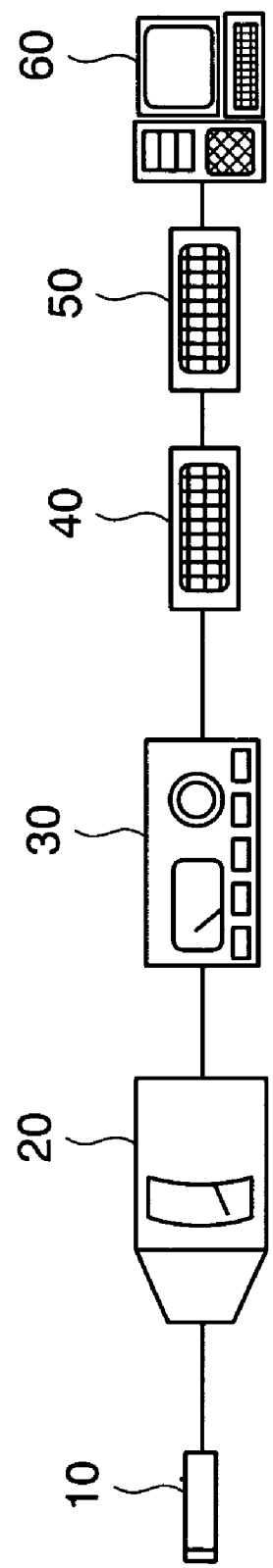
FIG. 1 is a block diagram explaining an example of the configuration of a sleep apnea syndrome diagnosing device according to an embodiment.
Figure 2:
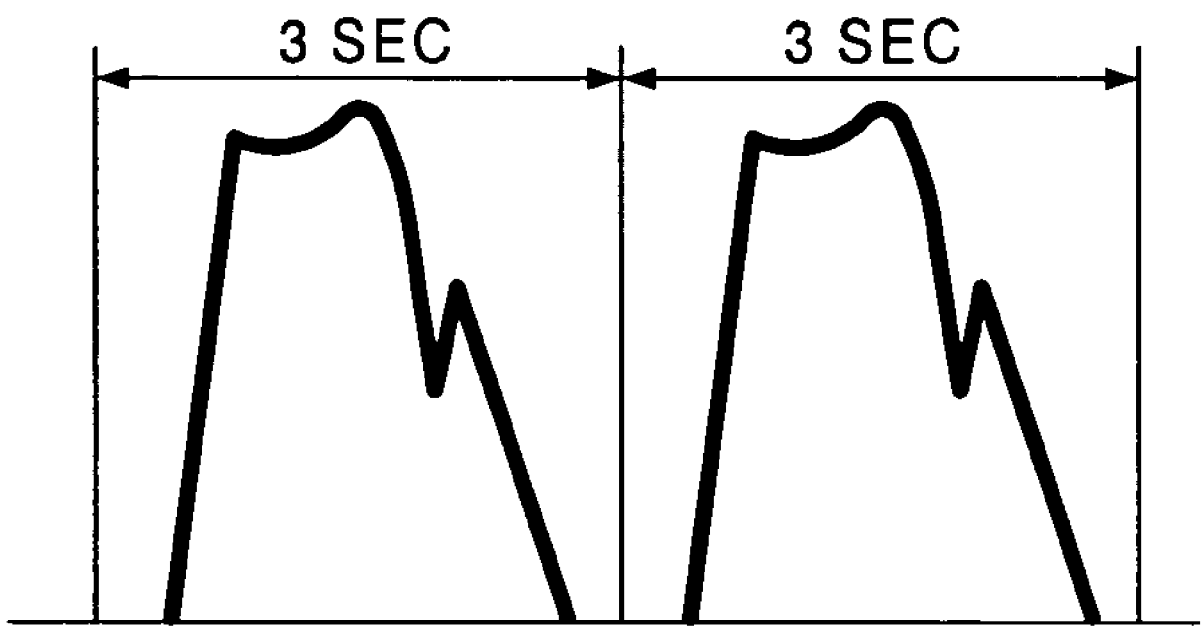
FIG. 2 is a diagram explaining a theory for calculating a correlation coefficient between a waveform of snoring sound of one cycle and a waveform of snoring sound of the next cycle in this embodiment.

FIG. 1 is a diagram showing an example of the configuration of a sleep apnea syndrome diagnosing device according to this embodiment. As shown in FIG. 1, the sleep apnea syndrome diagnosing device according to this embodiment includes a microphone 10, an amplifier 20, a low-pass filter 30, an analog to digital converter 40, a digital IO 50, and a computer 60.

The microphone 10 collects snoring sound of a patient who is sleeping, and converts the snoring sound to an analog electrical signal. This analog electrical signal is inputted to the amplifier 20. The analog electrical signal of the snoring sound inputted to the amplifier 20 is amplified and then inputted to the low-pass filter 30. A high frequency band (noise) is eliminated from the analog electrical signal inputted to the low-pass filter 30, and then the analog electrical signal is inputted to the analog to digital converter 40.

The analog electrical signal of the snoring sound is converted to a digital signal in the analog to digital converter 40, and inputted to the digital IO 50. The digital signal inputted from the digital IO 50 is inputted to the computer 60, where data on the digital signal is held and an analysis of the snoring sound is performed based on the held data. Then, a result of this analysis is displayed on a display or outputted from a printer.

Next, a snoring sound analyzing method performed by the computer 60 will be explained. The snoring sound accompanying breathing occurs regularly every time in synchronization with a breathing cycle. Therefore, after the collected snoring sound is averaged every 125 ms to find a sound pressure level, a waveform is cut out by a time window having a length corresponding to one cycle (about three seconds) of breathing of an ordinary person and used as reference data. Namely, in this embodiment, 125 ms is a sampling period of the snoring sound.

Subsequently, a waveform having one cycle length of breathing adjacent to the aforementioned waveform is cut out in the same manner and used as comparison data. A correlation coefficient between these reference data and comparison data is calculated. Such a computation is repeatedly performed along a time axis of the snoring sound to calculate a result thereof. If the snoring sound is repeated regularly accompanying the cycle of breathing, the value of the correlation coefficient calculated by such a computation shifts showing a numerical value very close to one. If hypopnea or apnea starts and thereby the snoring sound becomes irregular, the value of the correlation coefficient drops sharply at this point in time. Therefore, it is possible to keep track of changes in the snoring sound steadily by the value of correlation coefficient.

Note that the snoring sound is a biosignal, and there are temporal variations in the timing of its occurrence. Hence, even if the time axis of the snoring sound is cut out every time by the same time window to calculate a correlation coefficient, the value thereof varies. To exclude the influence thereof, in this embodiment, a six-second reference data moving period and a six-second comparison data moving period are provided, and correlation coefficients on all combinations are calculated while each shifting is performed by 125 ms each time with respect to a three-second breathing cycle. Namely, the reference data moving period which is longer than one cycle is set, and the comparison data moving period which is longer than one cycle is set as well.

Figure 3:
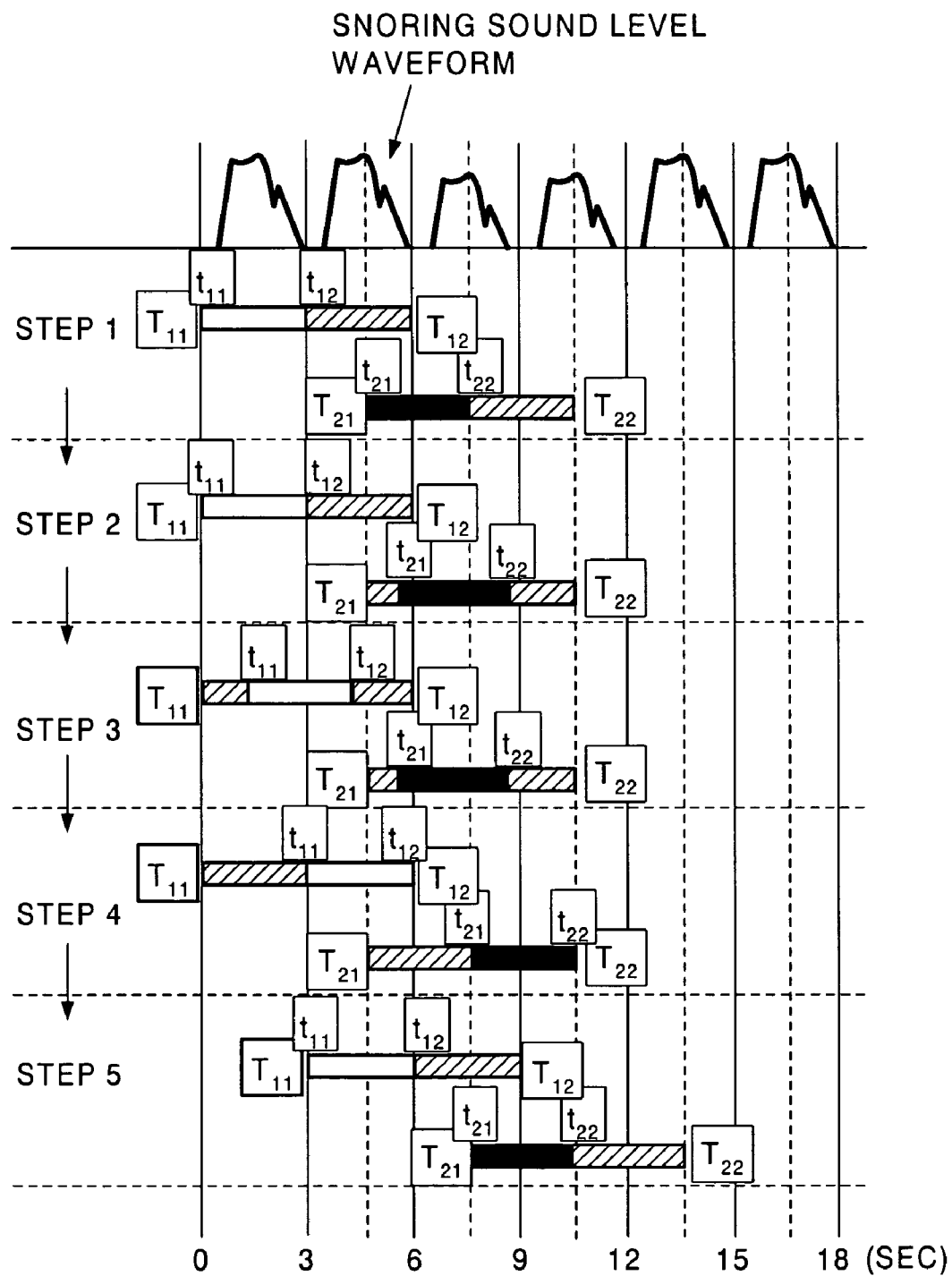
FIG. 3 is a diagram explaining a method according to this embodiment for calculating a correlation coefficient on snoring sound with irregular periodicity.

FIG. 3 is a diagram explaining this calculating method in detail. As shown in step 1 in FIG. 3, first, a three-second reference period $t_{11}$ to $t_{12}$ is set from time 0 sec which is a point 0. In this case, the six-second reference data moving period is between time 0 sec ($T_{11}$) and time 6 sec ($T_{12}$).

Next, a comparison period $t_{21}$ to $t_{22}$ is set, being shifted from the reference period $t_{11}$ to $t_{12}$ by 4.5 seconds. In this case, the comparison period is between time 4.5 sec ($t_{21}$) and time 7.5 sec ($t_{22}$), and the comparison data moving period is between time 4.5 sec ($T_{21}$) and time 10.5 sec ($T_{22}$). This comparison period $t_{21}$ to $t_{22}$ is set so as to overlap with the latter one fourth of the reference data moving period. Namely, the reference data moving period and the comparison data moving period overlap only by one fourth (1.5 seconds).

Then, a correlation coefficient between a waveform of the snoring sound of the reference period $t_{11}$ to $t_{12}$ and a waveform of the snoring sound of the comparison period $t_{21}$ to $t_{22}$ is calculated. An expression to calculate this correlation coefficient is shown by an expression (1). Here, it is assumed that there are n pieces of data between time $t_{11}$ and time $t_{12}$, and that there are n pieces of data between time $t_{21}$ and time $t_{22}$. In this embodiment, n=24. $x_i$ shows a data value of the i-th reference period, and $y_i$ shows a data value of the i-th comparison period. /x shows a mean value of data of the reference periods, and /y shows a mean value of data of the comparison periods.

$$r_{xy} = \frac{\sum_{i=1}^{n}(x_i - \overline{x})(y_i - \overline{y})/n}{\sqrt{\sum_{i=1}^{n}(x_i - \overline{x})^2/n}\sqrt{\sum_{i=1}^{n}(y_i - \overline{y})^2/n}} \qquad (1)$$

Next, as shown in step 2, in a state where the reference period $t_{11}$ to $t_{12}$ is fixed, while the comparison period $t_{21}$ to $t_{22}$ is being shifted by 125 ms each time, respective correlation coefficients between the waveform of the snoring sound of the reference period $t_{11}$ to $t_{12}$ and the waveform of the snoring sound of the comparison period $t_{21}$ to $t_{22}$ are calculated one by one. The comparison period $t_{21}$ to $t_{22}$ is shifted to the end of the comparison data moving period. In other words, the comparison period $t_{21}$ to $t_{22}$ is shifted until $t_{22}=T_{22}$ is attained. Accordingly, in this embodiment, 24 correlation coefficients are calculated with respect to one reference period $t_{11}$ to $t_{12}$. Incidentally, in this embodiment, the amount of shifting of the comparison period $t_{21}$ to $t_{22}$ is 125 ms, which corresponds to the sampling period of the snoring sound, but these two need not necessarily coincide with each other.

Next, as shown in FIG. 3, the process in step 2 is repeated while the reference period $t_{11}$ to $t_{12}$ is being shifted by 125 ms each time. In other words, the process in step 2 is performed while the reference period $t_{11}$ to $t_{12}$ is being shifted until $t_{12}=T_{12}$ is attained. Consequently, in this embodiment, 24×24=576 correlation coefficients are finally calculated. In step 4, positions of the reference period $t_{11}$ to $t_{12}$ and the comparison period $t_{21}$ to $t_{22}$ after 576 correlation coefficients are calculated are shown. Incidentally, in this embodiment, the amount of shifting of the reference period $t_{11}$ to $t_{12}$ is 125 ms, which corresponds to the sampling period of the snoring sound, but these two need not necessarily coincide with each other.

Next, a maximum value is extracted from values of the calculated 576 correlation coefficients and taken as a representative value. This representative value is adopted as a value of the correlation coefficient of the reference period $t_{11}$ to $t_{12}$. Then, both the reference period $t_{11}$ to $t_{12}$ and the comparison period $t_{21}$ to $t_{22}$ are shifted by three seconds, and the process from step 2 to step 4 is repeated. In this embodiment, by repeating the aforementioned process, the correlation coefficient between the snoring sound of one cycle and the snoring sound of the next cycle on the time axis is calculated sequentially.

Figure 4:
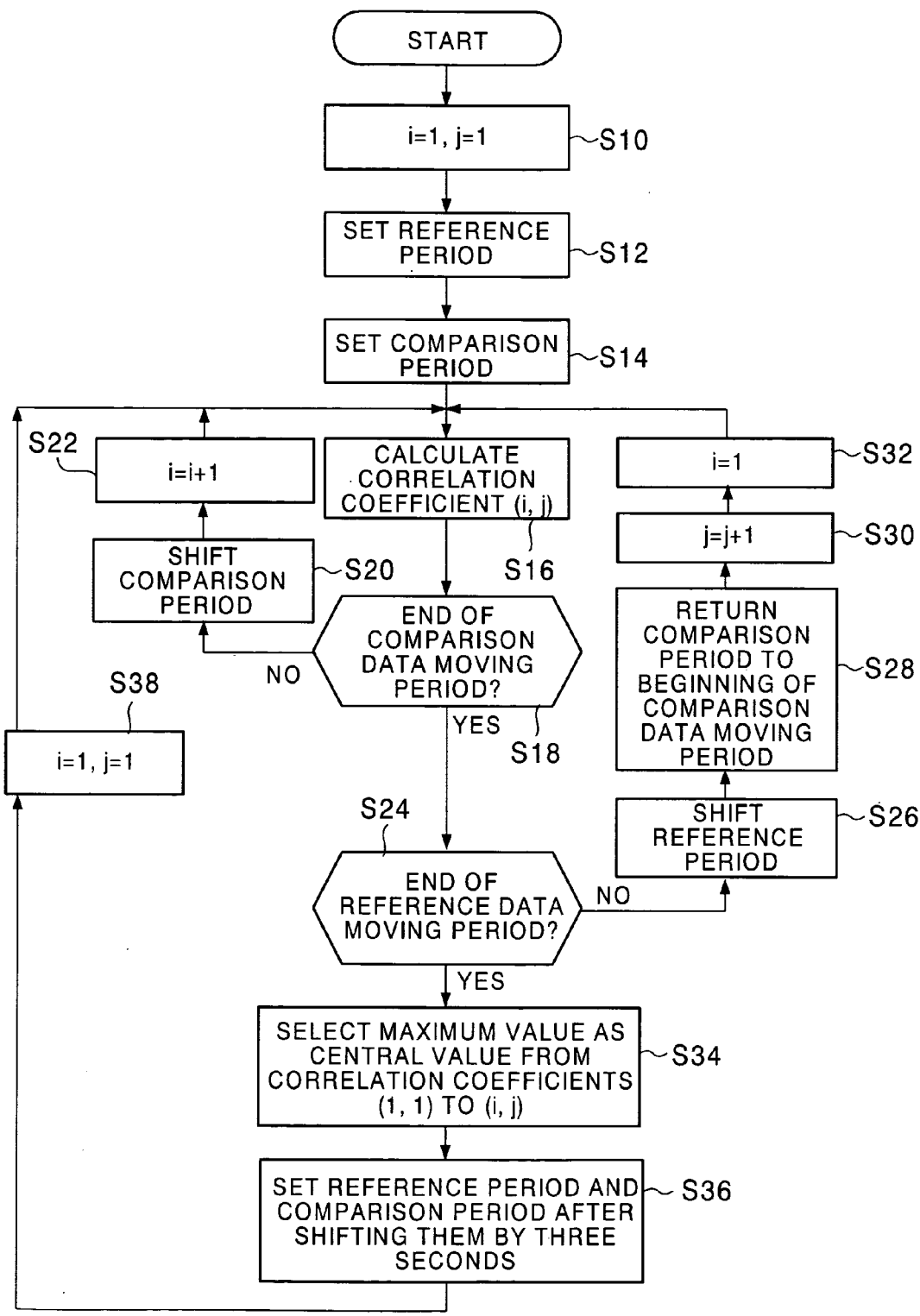
FIG. 4 is a flowchart explaining an analysis process of snoring sound executed by a computer according to this embodiment.

FIG. 4 shows a flowchart when the computer 60 performs the aforementioned correlation coefficient calculating process. As shown in FIG. 4, first, a variable i is initialized to one, and a variable j is also initialized to one (step S10). Subsequently, the three-second reference period $t_{11}$ to $t_{12}$ is set (step S12), and the three-second comparison period $t_{21}$ to $t_{22}$ is set (step S14). As described above, in this embodiment, the comparison period $t_{21}$ to $t_{22}$ is set at a position which is sifted from the reference period $t_{11}$ to $t_{12}$ by 4.5 seconds.

Next, a correlation coefficient [i, j] between a waveform of the snoring sound of the reference period $t_{11}$ to $t_{12}$ and a waveform of the snoring sound of the comparison period $t_{21}$ to $t_{22}$ is calculated (step S16). Subsequently, it is judged whether the comparison period $t_{21}$ to $t_{22}$ is the end of the comparison data moving period (step S18). When the comparison period $t_{21}$ to $t_{22}$ is not the end of the comparison data moving period (step S18: No), the comparison period $t_{21}$ to $t_{22}$ is shifted backward by 125 ms (step S20), one is added to the variable i (step S22), and the aforementioned process from step S16 is repeated.

On the other hand, when the comparison period $t_{21}$ to $t_{22}$ is the end of the comparison data moving period (step S18: Yes), it is judged whether the reference period $t_{11}$ to $t_{12}$ is the end of the reference data moving period (step S24). When the reference period $t_{11}$ to $t_{12}$ is not the end of the reference data moving period (step S24: No), the reference period $t_{11}$ to $t_{22}$ is shifted backward by 125 ms (step S26), and the comparison period $t_{21}$ to $t_{22}$ is returned to the beginning of the comparison data moving period (step S28). Then, one is added to the variable j (step S30), the variable i is initialized to one (step S32), and the aforementioned process from step S16 is repeated.

On the other hand, when the reference period $t_{11}$ to $t_{12}$ is the end of the reference data moving period (step S24: Yes), a maximum value is selected from values of the hitherto calculated correlation coefficients [1, 1] to [i, j] as a representative value of the correlation coefficients (step S34).

Next, the setting of the reference period $t_{11}$ to $t_{12}$ is shifted backward from the setting in step S12 by three seconds, and simultaneously the setting of the comparison period $t_{21}$ to $t_{22}$ is shifted backward from the setting in step S14 by three seconds (step S36). Subsequently, the variable i is initialized to one, simultaneously the variable j is initialized to one (step S38), and the aforementioned process from step S16 is repeated.

Figure 5:
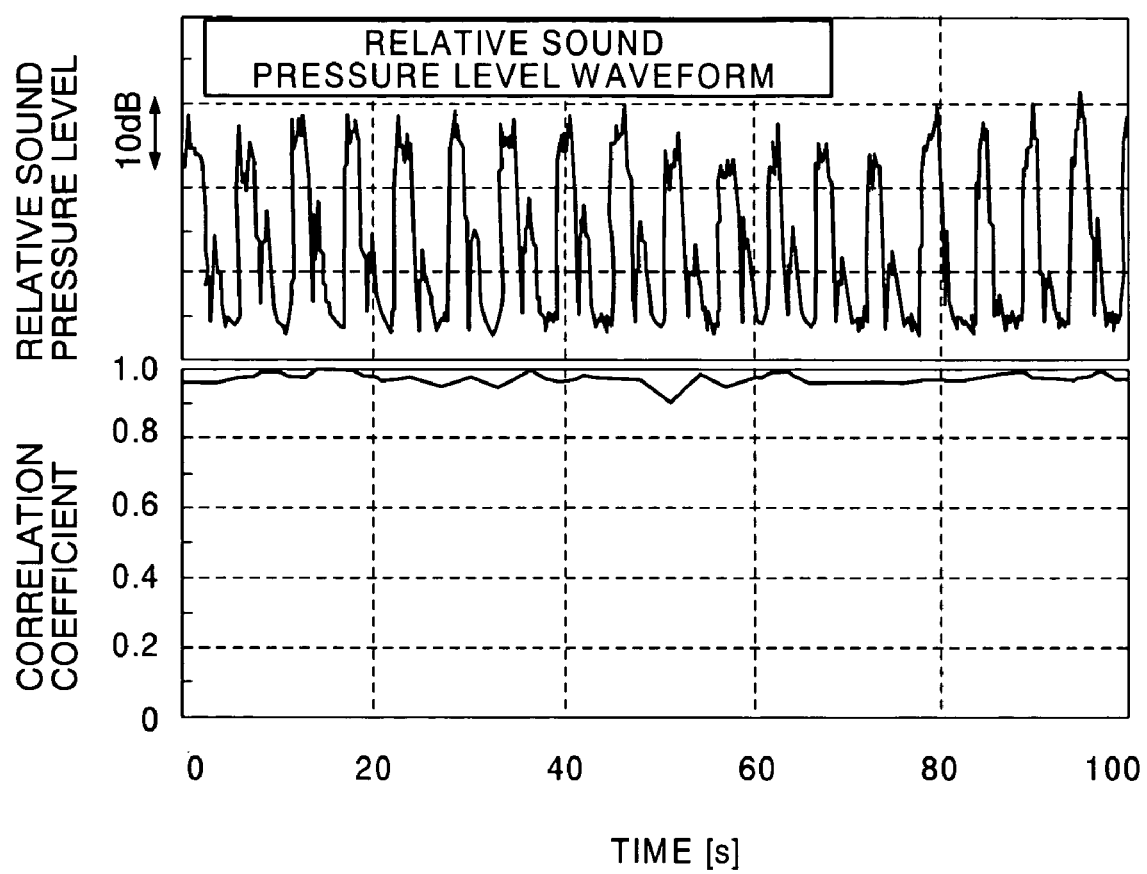
FIG. 5 is a graph showing a relative sound pressure level of snoring sound and its correlation coefficient when regular snoring sound continues.
Figure 6:
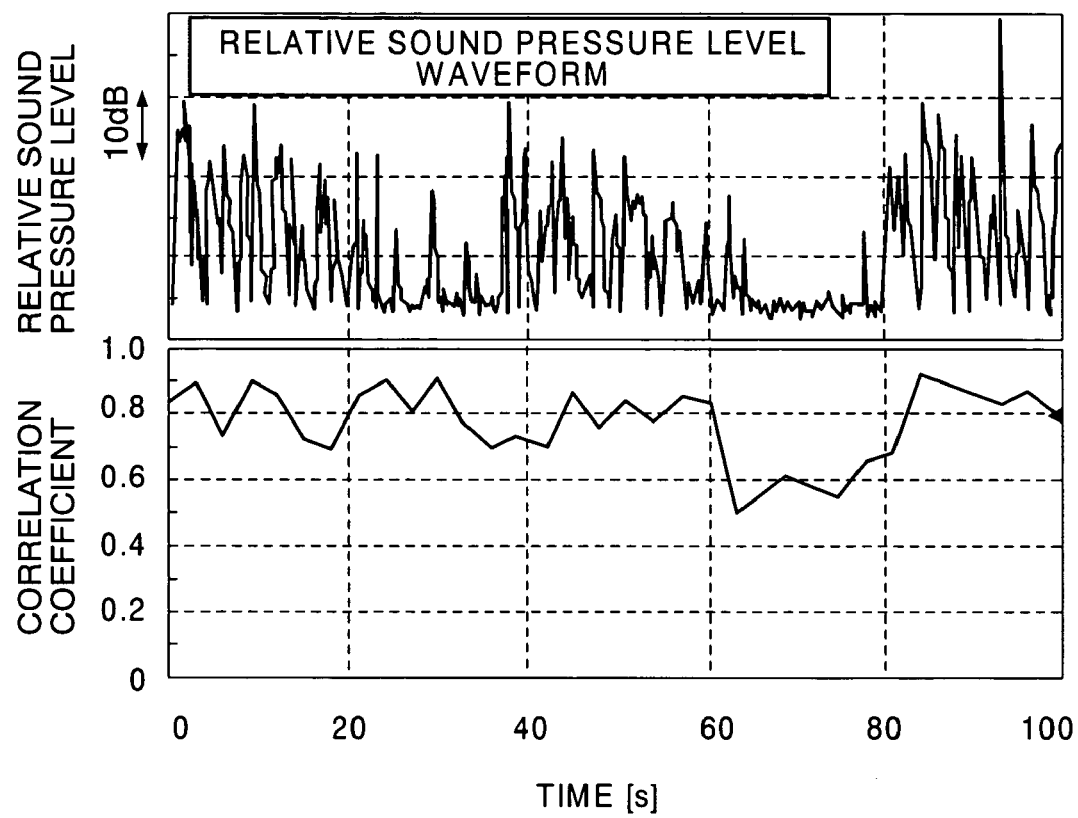
FIG. 6 is a diagram showing a relative sound pressure level of snoring sound and its correlation coefficient when hypopnea or apnea occurs.

FIG. 5 and FIG. 6 are graphs each showing an example of a diagnostic result by the sleep apnea syndrome diagnosing device according to this embodiment. FIG. 5 shows a graph of a relative sound pressure level waveform and its correlation coefficient when breathing is performed regularly, and FIG. 6 shows a graph of a relative sound pressure level waveform and its correlation coefficient when hypopnea or apnea occurs. In FIG. 5 and FIG. 6, when the sound pressure level waveform is calculated, a one octave band-pass filter process (BPF process) is performed at a center frequency of 1 kHz with consideration given to characteristics of a snoring sound spectrum and an acoustic characteristic in a room where the snoring sound is collected.

As shown in FIG. 5, when the snoring sound is produced regularly with breathing, the correlation coefficient shifts, showing a value close to one. On the other hand, as shown in FIG. 6, when hypopnea or apnea occurs, the correlation coefficient shifts, showing an irregular value lower than one. Namely, in FIG. 6, as shown by the relative sound pressure level waveform, breathing appears to be stopped for 15 seconds from time 65 sec to time 80 sec, and correlation coefficient values during this period are approximately 0.6, which is lower than correlation coefficient values at other times. Moreover, it tunes out that correlation coefficient values are low at times other than this period, and that breathing is irregular.

As described above, according to the sleep apnea syndrome diagnosing device of this embodiment, snoring sound of a patient is collected by the microphone 10 and analyzed using the computer 60, which makes it possible to save time and labor required for a diagnosis of sleep apnea syndrome, resulting in cost reduction. More specifically, regarding the collected snoring sound, a correlation coefficient between one cycle and the next cycle is calculated, and thereby it becomes possible to express irregularities in the snoring sound numerically and perform a diagnosis, which hitherto depends on a medical specialist's analysis, by using the computer 60.

Moreover, with respect to the three-second reference period, the six-second reference data moving period which is longer than the three-second reference period is set, and with respect to the three-second comparison period, the six-second comparison data moving period which is longer than the three-second comparison period is set. Simultaneously, correlation coefficients are calculated on all combinations of reference periods set by shifting in the reference data moving period by 125 ms each time and comparison periods set by shifting in the comparison data moving period by 125 ms each time, and a maximum value thereof is adopted as a correlation coefficient of the reference period. Accordingly, even in the case of snoring sound with irregular periodicity, it is possible to appropriately set a time window and calculate a correlation coefficient.

It should be mentioned that the present invention is not limited to the aforementioned embodiment, and various changes may be made therein. For example, the result of the analysis process by the computer 60 is outputted in graphical form in the aforementioned embodiment, but the output form thereof is not limited to a graph. For example, a list of correlation coefficients may be outputted in numerical form to a printer, and when the analysis result contains correlation coefficients of 0.6 or less, a warning may be displayed on a display of the computer 60.

Moreover, the numerical values of time and length used in the aforementioned embodiment are all just examples, and the time and length are not limited to these numerical values. Further, the reference data moving period and the comparison data moving period need not necessarily have the same length, and the amount of shifting of the reference period in the reference data moving period and the amount of shifting of the comparison period in the comparison data moving period need not necessarily have the same length.

Furthermore, the present invention is applicable not only to a diagnosis of sleep apnea syndrome but also to diagnoses of diseases using other biosounds. For example, by collecting heart sound and subjecting data on this heart sound to the aforementioned analysis process, diseases such as arrhythmia can be diagnosed.

Additionally, the application of the present invention is not limited to signal data acquired from a living human body, and its application to an analysis of signal data with irregular periodicity is possible. For example, it is also possible to collect data on rotation sound of a gear wheel and subject the data to the aforementioned analysis process to thereby detect a defect and the like in the gear wheel.

Figure 7:
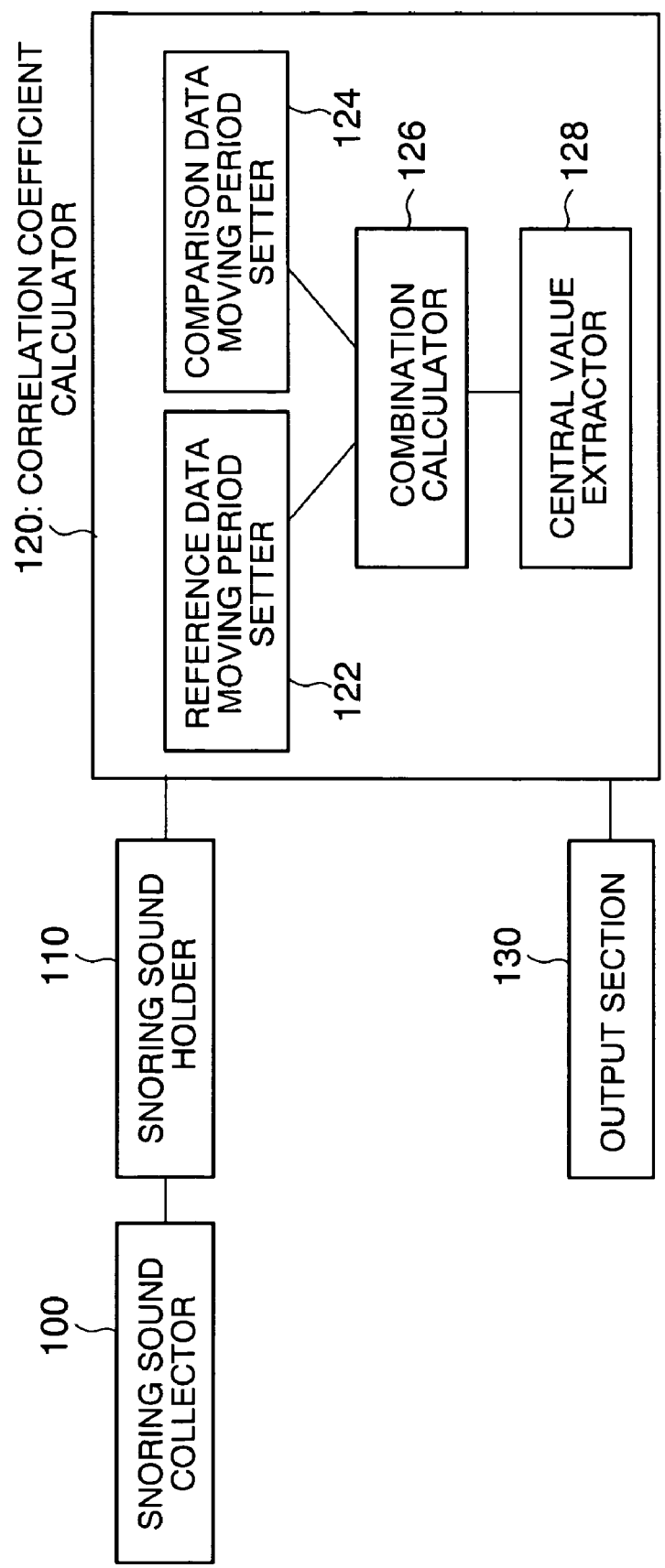
FIG. 7 is a diagram showing the configuration of a sleep apnea syndrome diagnosing device when the analysis process of snoring sound according to this embodiment is realized by hardware.

Moreover, the correlation coefficient calculating process is realized by software processing of the computer 60 in the aforementioned embodiment, but it can be realized by hardware processing. FIG. 7 is a block diagram showing the configuration of a sleep apnea diagnosing device when the aforementioned correlation coefficient calculating process is realized by hardware processing.

As shown in FIG. 7, snoring sound of a patient is collected by a snoring sound collector 100 composed of the microphone 10 and held in a snoring sound holder 110. The snoring sound holder 110 is composed, for example, of a volatile semiconductor memory device.

A correlation coefficient calculator 120 divides a time axis of the snoring sound held in the snoring sound holder 110 into plural cycles and calculates a correlation coefficient between the snoring sound of one cycle and the snoring sound of a cycle next to the one cycle in sequence. An output section 130 outputs the correlation coefficient calculated by the correlation coefficient calculator 120. In the aforementioned embodiment, one cycle is set to about three seconds.

More specifically, the correlation coefficient calculator 120 includes a reference data moving period setter 122, a comparison data moving period setter 124, a combination calculator 126, and a representative value extractor 128. The reference data moving period setter 122 sets a reference data moving period having a first length longer than a length of the aforementioned cycle on the time axis of the snoring sound. The comparison data moving period setter 124 sets a comparison data moving period having a second length longer than the length of the aforementioned cycle on the time axis of the snoring sound, the comparison data moving period being shifted from the reference data moving period by a first predetermined period. In the aforementioned embodiment, the reference data moving period having the first length is set to six seconds, and the comparison data moving period having the second length is also set to six seconds. The first predetermined period by which the shifting is to be performed is set to 4.5 seconds.

The combination calculator 126 calculates correlation coefficients respectively on combinations of cycles set by shifting in the reference data moving period by a second predetermined period each time and cycles set by shifting in the comparison data moving period by a third predetermined period each time. The representative value extractor 128 extracts a representative value based on the correlation coefficients calculated by the combination calculator 126.

In this case, the combination calculator 126 calculates correlation coefficients on all the combinations of the cycles set by shifting in the reference data moving period by the second predetermined period each time and the cycles set by shifting in the comparison data moving period by the third predetermined period each time.

The representative value extractor 128 extracts a maximum value from values of the correlation coefficients calculated by the combination calculator 128 as the representative value.

The aforementioned second predetermined period and third predetermined period may coincide with a data sampling period of the snoring sound held in the snoring sound holder 110. In the aforementioned embodiment, both the second predetermined period and the third predetermined period are 125 ms.

The output section 130 can also output the correlation coefficients calculated by the combination calculator 126 as a graph.

Besides, as for the analysis process by the computer 60 explained in the aforementioned embodiment, it is possible to record a program to execute this analysis process on a record medium such as a flexible disk, a CD-ROM (Compact Disc-Read Only Memory), a ROM, a memory card, or the like and distribute this program in the form of the record medium. In this case, the aforementioned embodiment can be realized by making the computer 60 read the record medium on which this program is recorded and execute this program.

Moreover, the computer 60 sometimes has other programs such as an operating system, other application programs, and the like. In this case, by using these other programs in the computer 60, a command, which calls a program to realize a process equal to that in the aforementioned embodiment out of programs in the computer 60, may be recorded on the record medium.

Further, such a program can be distributed not in the form of the record medium but in the form of a carrier wave via a network. The program transmitted in the form of the carrier wave over the network is incorporated in the computer 60, and the aforementioned embodiment can be realized by executing this program.

Furthermore, when being recorded on the record medium or transmitted as the carrier wave over the network, the program is sometimes encrypted or compressed. In this case, the computer 60 which has read the program from the record medium or the carrier wave needs to execute the program after decrypting or expanding it.

The invention claimed is:

1. A sleep apnea syndrome diagnosing device, comprising:
   a snoring sound collector which collects snoring sound;
   a snoring sound holder which holds the collected snoring sound;
   a correlation coefficient calculator which divides a time axis of the snoring sound held in the snoring sound holder into plural cycles and which sequentially calculates a correlation coefficient between the snoring sound of one cycle and the snoring sound of a cycle next to the one cycle; and
   an output section which outputs the correlation coefficient calculated by the correlation coefficient calculator,
   wherein the correlation coefficient calculator comprises:
   a reference data moving period setter which sets a reference data moving period having a first length longer than a length of the cycle on the time axis of the snoring sound;
   a comparison data moving period setter which sets a comparison data moving period having a second length longer than the length of the cycle on the time axis of the snoring sound, the comparison data moving period being shifted from the reference data moving period by a first predetermined period;

a combination calculator which calculates correlation coefficients respectively on combinations of cycles set by shifting within the reference data moving period by a second predetermined period each time and cycles set by shifting within the comparison data moving period by a third predetermined period each time; and a representative value extractor which extracts a representative value based on the correlation coefficients calculated by the combination calculator, wherein the combination calculator calculates correlation coefficients on all the combinations of the cycles set by shifting within the reference data moving period by the second predetermined period each time and the cycles set by shifting within the comparison data moving period by the third predetermined period each time.

2. The sleep apnea syndrome diagnosing device according to claim 1, wherein the representative value extractor extracts a maximum value from values of the correlation coefficients calculated by the combination calculator as the representative value.

3. The sleep apnea syndrome diagnosing device according to claim 2, wherein the second predetermined period and the third predetermined period coincide with a data sampling period of the snoring sound held in the snoring sound holder.

4. The sleep apnea syndrome diagnosing device according to claim 1, wherein the output section outputs the correlation coefficients calculated by the combination calculator as a graph.

5. A sleep apnea syndrome diagnosing method, comprising the steps of:

collecting snoring sound and storing the collected snoring sound in a snoring sound holder;

dividing a time axis of the snoring sound held in the snoring sound holder into plural cycles;

sequentially calculating a correlation coefficient between the snoring sound of one cycle and the snoring sound of a cycle next to the one cycle; and outputting the calculated correlation coefficient; and diagnosing a sleep apnea syndrome based on the outputted correlation coefficient, wherein the step of calculating the correlation coefficient comprises the steps of:

setting a reference data moving period having a first length longer than a length of the cycle on the time axis of the snoring sound;

setting a comparison data moving period having a second length longer than the length of the cycle on the time axis of the snoring sound, the comparison data moving period being shifted from the reference data moving period by a first predetermined period;

calculating correlation coefficients on respective combinations of cycles set by shifting within the reference data moving period by a second predetermined period each time and cycles set by shifting within the comparison data moving period by a third predetermined period each time; and extracting a representative value based on the calculated correlation coefficients, wherein in the step of calculating the correlation coefficients on the respective combinations, the correlation coefficients are calculated on all the combinations of the cycles set by shifting within the reference data moving period by the second predetermined period each time and the cycles set by shifting within the comparison data moving period by the third predetermined period each time.

6. The sleep apnea syndrome diagnosing method according to claim 5, wherein in the step of extracting the representative value, a maximum value is extracted from values of the calculated correlation coefficients as the representative value.

7. The sleep apnea syndrome diagnosing method according to claim 6, wherein the second predetermined period and the third predetermined period coincide with a data sampling period of the snoring sound held in the snoring sound holder.

8. The sleep apnea syndrome diagnosing method according to claim 5, wherein in the step of outputting the calculated correlation coefficient, the calculated correlation coefficients are outputted as a graph.

9. A computer program product including a tangible computer readable medium for diagnosing sleep apnea syndrome, the program being operable to cause a computer to execute the steps of:

collecting snoring sound and storing the collected snoring sound in a snoring sound holder;

dividing a time axis of the snoring sound held in the snoring sound holder into plural cycles;

sequentially calculating a correlation coefficient between the snoring sound of one cycle and the snoring sound of a cycle next to the one cycle; and outputting the calculated correlation coefficients, wherein the step of calculating the correlation coefficient comprises the steps of:

setting a reference data moving period having a first length longer than a length of the cycle on the time axis of the snoring sound;

setting a comparison data moving period having a second length longer than the length of the cycle on the time axis of the snoring sound, the comparison data moving period being shifted from the reference data moving period by a first predetermined period;

calculating correlation coefficients on respective combinations of cycles set by shifting within the reference data moving period by a second predetermined period each time and cycles set by shifting within the comparison data moving period by a third predetermined period each time; and extracting a representative value based on the calculated correlation coefficients.

10. A signal analyzer, comprising:

a signal data holder which holds signal data with irregular periodicity;

a correlation coefficient calculator which divides a time axis of the signal data held in the signal data holder into plural cycles and sequentially calculating a correlation coefficient between the signal data of one cycle and the signal data of a cycle next to the one cycle; and an output section which outputs the correlation coefficient calculated by the correlation coefficient calculator, wherein the correlation coefficient calculator comprises;

a reference data moving period setter which sets a reference data moving period having a first length longer than a length of the cycle on the time axis of the signal data;

a comparison data moving period setter which sets a comparison data moving period having a second length longer than the length of the cycle on the time axis of the signal data, the comparison data moving period being shifted from the reference data moving period by a first predetermined period;

a combination calculator which calculates correlation coefficients respectively on combinations of cycles set by shifting within the reference data moving period by a second predetermined period each time and cycles set by shifting within the comparison data moving period by a third predetermined period each time; and a representative value extractor which extracts a representative value based on the correlation coefficients calculated by the combination calculator.

11. A signal analyzing method, comprising the steps of:

collecting signal data with irregular periodicity and holding the signal data in a signal data holder;

dividing a time axis of the signal data held in the signal data holder into plural cycles;

sequentially calculating a correlation coefficient between the signal data of one cycle and the signal data of a cycle next to the one cycle; and outputting the calculated correlation coefficient;

and analyzing the outputted correlation coefficient, wherein the step of calculating the correlation coefficient comprises the steps of;

setting a reference data moving period having a first length longer than a length of the cycle on the time axis of the signal data;

setting a comparison data moving period having a second length longer than the length of the cycle on the time axis of the signal data, the comparison data moving period being shifted from the reference data moving period by a first predetermined period;

calculating correlation coefficients on respective combinations of cycles set by shifting within the reference data moving period by a second predetermined period each time and cycles set by shifting within the comparison data moving period by a third predetermined period each time; and extracting a representative value based on the calculated correlation coefficients.

* * * * *